United States Patent [19]

McGinnis et al.

[11] 4,313,017

[45] Jan. 26, 1982

[54] SELECTIVE HYDROGENATION OF POLYNUCLEAR AROMATIC REACTANTS

[75] Inventors: Roger N. McGinnis; Lloyd E. Gardner; Floyd Farha, Jr., all of Bartlesville, Okla.

[73] Assignee: Phillips Petroleum Co., Bartlesville, Okla.

[21] Appl. No.: 221,121

[22] Filed: Dec. 29, 1980

Related U.S. Application Data

[63] Continuation of Ser. No. 118,834, Feb. 5, 1980, abandoned.

[51] Int. Cl.$^3$ ................................................ C07C 5/10
[52] U.S. Cl. ...................................... 585/266; 585/268; 585/271; 585/275; 252/475; 423/598
[58] Field of Search ............... 585/268, 271, 275, 661, 585/266; 423/598; 252/475

[56] References Cited

U.S. PATENT DOCUMENTS

| | | | |
|---|---|---|---|
| 2,279,198 | 4/1942 | Hoppke | 252/475 |
| 2,992,931 | 7/1961 | Merker | 423/598 |
| 3,794,717 | 2/1974 | Miyatuka | 423/598 |
| 3,883,566 | 5/1975 | Johnson et al. | 585/275 |
| 3,920,745 | 11/1975 | Floriani et al. | 585/275 |
| 4,059,628 | 11/1977 | Del Pesco et al. | 252/475 |
| 4,061,583 | 12/1977 | Murata et al. | 423/598 |
| 4,144,277 | 3/1979 | Walker et al. | 260/666 A |
| 4,173,485 | 11/1979 | Woditsch et al. | 423/598 |
| 4,176,140 | 11/1978 | Bertus et al. | 585/661 |
| 4,218,346 | 8/1980 | Walker et al. | 252/475 |
| 4,228,040 | 10/1980 | Bertus et al. | 252/475 |

*Primary Examiner*—Arthur P. Demers

[57] ABSTRACT

Polynuclear aromatic reactants are selectively hydrogenated in the presence of hydrogen gas with a zinc titanate catalyst.

29 Claims, No Drawings

SELECTIVE HYDROGENATION OF POLYNUCLEAR AROMATIC REACTANTS

This is a continuation of application Ser. No. 118,834, filed Feb. 5, 1980, now abandoned.

This invention relates to the selective hydrogenation of polynuclear aromatic reactants. In another aspect the invention relates to the use of a zinc titanate catalyst system.

Selective hydrogenation processes for the conversion of polynuclear aromatic reactants to products having a higher degree of saturation are well known. Some suitable examples are naphthalene, anthracene, phenanthrene pyrene and naphthacene. Selectively hydrogenated polynuclear aromatic compounds such as those noted above are effective sources of hydrogen to solubilize coal in coal liquefaction processes. Selective hydrogenation processes are also useful in converting the polynuclear aromatics in heavy cycle oil, in heavy gas oil and in coal tar into mononuclear aromatics and in obtaining maximum yields thereof. It is therefore an object of this invention to provide a process for selectively hydrogenating the more readily reducible rings in a polynuclear aromatic reactant in the presence of a catalyst.

Other objects and advantages of the invention will be apparent from the foregoing brief description of the invention and the appended claims as well as from the detailed description of the invention as described herein.

In accordance with the present invention, a polynuclear aromatic reactant is contacted with a zinc titanate catalyst under conditions to selectively hydrogenate the reactant. The zinc titanate catalyst employed in the present invention is modified with a promoter to improve the selective hydrogenation process.

The reactants which can be selectively hydrogenated in accordance with the present invention are polynuclear aromatic reactants having at least two aromatic nuclei and wherein at least two of the aromatic nuclei have two common carbon atoms. Some suitable reactants include naphthalene, anthracene, phenanthrene, pyrene and naphthacene. Also suitable are mixtures that contain these compounds or compounds that contain their derivatives, including petroleum refinery streams such as vacuum gas oil, cycle oil, extract oil liquids derived from coal tar, and aromatic compounds having heteroatoms attached thereto, i.e., nitrogen, oxygen and sulfur. Polynuclear aromatic reactants which can be selectively hydrogenated in accordance with this invention will frequently have from 10 to 40 carbon atoms. Normally polynuclear aromatic reactants having more than 40 carbon atoms per molecule are not used because it has been determined that polynuclear aromatic compounds having more than 40 carbon atoms resist being placed in solution. The preferred range will have 10 to 20 carbon atoms; their average molecular weight is within the range of from 140 to 560. At present, the preferred reactant is phenanthrene.

The catalyst employed in the selective hydrogenation process of the present invention is a calcined composition of zinc, titanium, and sufficient oxygen to satisfy the valence requirements of the zinc and titanium. The atomic ratio of zinc to titanium is within the range of from 1:1 to 3:1, preferably within the range of from 1.8:1 to 2:1 because it increases the activity and imparts the desired selectivity for this hydrogenation process. The preferred form of the catalyst is zinc orthotitanate.

The catalyst can be prepared by any suitable method such as by intimately mixing suitable portions of zinc oxide and titanium dioxide, preferably in water, and calcining the mixture in the presence of free oxygen at a temperature in the range of from 650° to 1050° C., preferably within the range of from 675° to 975° C. because within this temperature range the surface area of the catalyst is maintained and sintering of the catalyst is minimized. This allows a higher production rate at a cost that is economically feasible. It is presently preferred that the titanium dioxide used in preparing the catalyst have an average particle size of less than 100 millimicrons, preferably less than 30 millimicrons, since this particle size reacts readily with the zinc oxide which results in a more active catalyst.

The catalyst can also be prepared by coprecipitation from solutions of a zinc compound and a titanium compound. The solutions are mixed together and the hydroxides are precipitated by the addition of ammonium hydroxide. The precipitate is then washed and dried and then calcined as described above.

In addition to using the zinc titanate catalyst alone, a promoter can be used with the zinc titanate generally with improved results. Suitable promoters include vanadium, chromium, cobalt, nickel, molybdenum, tungsten, rhenium, platinum and any combination of any two or more thereof. The promoter is generally used in a form which is convertible to the oxide on calcination and thus is generally present on the catalyst in the oxide form.

Some vanadium compounds suitable for use as a promoter include di-, tri-, tetra-, and pentavalent vanadium oxides, vanadium (III) sulfide, vanadium (IV) oxide sulfate, ammonium metavanadate, sodium metavanadate, and the like.

Some chromium compounds suitable for use as a promoter include ammonium chromate and ammonium dichromate, chromic nitrate, chromium (III) oxide, chromium (VI) oxide, chromic sulfate, potassium chromate and potassium dichromate, chromic acetate, and the like.

Some nickel compounds suitable for use as a promoter include nickel acetate, nickel carbonate, nickel nitrate, nickel oxide, nickel sulfate, ammonium nickel sulfate, nickel sulfamate, and the like.

Some molybdenum compounds suitable for use as a promoter include ammonium molybdate, ammonium heptamolybdate, sodium molybdate, potassium molybdate, molybdenum oxides such as molybdenum (IV) oxide and molybdenum (VI) oxide, molybdenum sulfide, and the like.

Some tungsten compounds suitable for use as a promoter include ammonium tungstates such as ammonium metatungstate and ammonium paratungstate, tungsten oxides such as tungsten (IV) oxide and tungsten (VI) oxide, tungsten sulfides such as tungsten (IV) sulfide and tungsten (VI) sulfide, heteropolyacids such as tungstophosphoric acid and tungstosilicic acid, and the like.

Some rhenium compounds suitable for use as a promoter include perrhenic acid, ammonium perrhenate, rhenium oxides such as rhenium (VI) oxide and rhenium (VII) oxide, rhenium sulfide, and the like.

Some platinum compounds suitable for use as a promoter include diamine platinum (II) nitrate, tetraamine platinum (II) nitrate, and the like.

In addition to the above recited compounds, halogen-containing compounds of these promoters are substantially equivalent to the compounds listed, and may be employed as promoters. However, the user should be aware of the possibility of corrosion of process equipment caused by their presence.

At present, the catalyst comprising rhenium on zinc titanate is preferred for the selective hydrogenation of polynuclear aromatic reactants because the products obtained from runs where rhenium was the promoter clearly demonstrate a high degree of selectivity.

The promoter can be applied to the zinc titanate as finely divided solids and dispersed by any method known in the art including rolling, shaking, or stirring. The preferred method of adding the promoter to the zinc titanate is to impregnate the zinc titanate catalyst with a solution that contains the promoting element as a compound such as an aqueous solution of ammonium perrhenate. When the promoter is impregnated on the zinc titanate catalyst in this manner, the impregnated catalyst should be dried to remove the solvent, then heated in air to about 540° C. (1000° F.) before using the promoter for selective hydrogenation. Where more than one promoter is used, the zinc titanate catalyst should be dried and calcined after each addition. The drying and calcining procedures are important for two reasons: (1) drying removes the solvent; and (2) calcining converts the promoter to an oxide. The benefits of the calcining step are realized when two or more incompatible promoters must be placed on the catalyst before it can be used in the selective hydrogenation process. For example, when promoter compounds such as nickel nitrate and sodium metavanadate are put in solution together without first converting one to an oxide, a precipitate results. This prevents complete dispersion of the promoter on the catalyst and intereferes with the hydrogenation process since part of the surface area of the catalyst will be void of any promoter. Therefore, unless the above steps are strictly practiced, the cost of producing selectively hydrogenated products is substantially increased.

The composition of the promoted catalyst comprises zinc titanate plus any one of the promoting elements or any combination of two or more thereof with the total amount of the promoting elements selected over a broad range. Generally, the total weight of all promoters used in the present invention, expressed as an element and based on the total weight of the zinc titanate catalyst plus promoter, is within the range of from 0.1 to 24 weight percent. Within the limits cited for the total weight of the zinc titanate catalyst plus promoters, the usual concentration of any single promoter, expressed as an element and based on the total weight of catalyst plus promoter, is generally within the range of from 0.1 to 16 weight percent; the preferred concentration of any single promoter is generally within the range of from 1.6 to 8 weight percent because the products obtained therefrom demonstrate high selectivity. The preferred concentration of rhenium and platinum is within the range of from 0.05 to 2 weight percent. This concentration range is not critical to the performance of rhenium and platinum; however, the range is chosen to minimize the total cost of the catalyst when rhenium and platinum are used as promoters. After the preparation of a catalyst plus promoter, it is ready for use in a selective hydrogenation process.

The selective hydrogenation process of this invention can be carried out by means of any apparatus whereby there is achieved the combining of the reactant with the hydrogen gas for contact with the catalyst. The reactant and the hydrogen gas can both pass together through the catalyst in upflow, or in downflow, or in countercurrent flow with hydrogen gas moving upward and the reactant moving downward. The process of this invention can be effected over a fixed catalyst bed, fluidized catalyst bed or a moving catalyst bed. A fixed catalyst bed is preferred because it facilitates the separation of the liquids from the solid catalyst and increases the life of the catalyst.

Any suitable hydrogenation temperature can be employed which provides the desired degree of catalytic activity in the selective hydrogenation of the reactant. The selective hydrogenation temperature will be in the range of from 149° to 538° C. (300° to 1000° F.) and will more preferably be in the range of from 204° to 371° C. (400° to 700° F.) because it has been determined that temperatures above this range will result in undesirable reactions and cause nonselective products to be produced.

Any suitable pressure can be utilized for selective hydrogenation. The selective hydrogenation pressure will be in the range of from $1.48 \times 10^6$ to $20.8 \times 10^6$ Pascals (Pa). This pressure represents a partial pressure of the reactant plus the partial pressure of the hydrogen gas used for selective hydrogenation. Preferably, the pressure should be within the range of from $2.86 \times 10^6$ to $6.9 \times 10^6$ Pascals because the products obtained within this pressure range demonstrate a high degree of selectivity.

Any suitable quantity of hydrogen can be combined with the reactant which imparts the desired degree of catalytic activity in the selective hydrogenation of the reactant. The quantity of hydrogen to be combined with the reactant is generally within the range of from 100 to 10,000 standard cubic feet per barrel (SCF/bbl) and will more preferably be within the range of from 500 to 3,000 SCF/bbl. A barrel is equivalent to 42 gallons.

The selective hydrogenation process can be carried out at any contact time of the reactant with the catalyst which provides a selectively hydrogenated product. The contact time of the reactant with the catalyst expressed as volume of a liquid per volume of catalyst per hour (LHSV) is generally within the range of from 0.1 to 20. Preferably, the contact time is within the range of from 0.5 to 5 LHSV because this range normally assures adequate time for the selective hydrogenation reaction to take place.

In order to restore the activity of the catalyst it may be necessary to periodically dispose of carbonaceous deposits by combustion. The regeneration of the catalyst can be effected by treating the used catalyst with free oxygen containing gas. Air or diluted air are preferred. The temperature of the catalyst should not exceed about 540° C. (1000° F.) during the regeneration to avoid damaging the catalyst by sintering or by removing volatile promoters.

The following examples are presented in further illustration of the invention.

Catalyst Preparation

Zinc orthotitanate was prepared by combining 162.8 grams (g) (2 moles) of Mallinckrodt zinc oxide with 79.9 g (1 mole) of Cab-O-Ti (Cabot Corporation) titanium dioxide in 1200 milliliters (mL) of water and mixing for ten minutes in a blender. The resulting slurry was dried in an oven at 105° C., then calcined by heating in air at 816° C. for three hours. After cooling the solid it was crushed and screened; the −20+40 United States sieve series fraction was treated with rhenium.

Catalyst A was prepared by impregnating 50.3 g (56 mL) of zinc titanate prepared above with 44 mL of 0.14 molar aqueous ammonium perrhenate. After drying under a heat lamp to remove the water the residue was calcined in a muffle furnace in air for an hour at 538° C. The finished catalyst contained, by calculation, 2.0 weight percent of rhenium as rhenium oxide.

Catalyst B was prepared by impregnating 40 g of zinc titanate prepared above with a solution obtained by diluting 2 mL of 0.149 molar ammonium perrhenate to about 40 mL with water. Water was removed by drying in an oven and the residue was calcined in a muffle furnace in air for an hour at 538° C. The finished catalyst contained, by calculation, 0.15 weight percent rhenium as rhenium oxide.

Example I (Runs 1-14)

Catalysts A and B were used in runs in which phenanthrene was hydrogenated. The runs were made using a reactor made of 316 stainless steel tubing. It was three-fourth inch outside diameter (o.d.)×12 inches long and contained a three-sixteenth inch o.d. thermowell. 20 mL of catalyst covered with 20 mL of alpha alumina were used. The reactor was used in an electrically heated, temperature controlled furnace. Runs were made downflow, in trickle bed mode. Hydrogen was metered with a differential pressure cell, phenanthrene dissolved in benzene was pumped with a calibrated pump, and reaction pressure was controlled with a back pressure regulator. Liquid product was collected in a cooled trap and effluent gas was measured with a gas meter, then vented. Liquid product was collected for thirty or sixty minute intervals, and the samples thus obtained were analyzed by gas liquid chromatography (GLC) using an OV-101 silicone capillary column.

Table I summarizes results from the runs with catalyst A. The runs were made at $3.55 \times 10^6$ Pa (500 psig) with feedstock comprising a 15 weight percent solution of phenanthrene in benzene. The feed rate was 1.0 volume of liquid per volume of catalyst per hour (LHSV) based on the solution, i.e., 0.15 LHSV based on phenanthrene only. Between samples 6 and 7 the run was stopped and the reactor was permitted to cool overnight, but hydrogen pressure was maintained on the reactor.

TABLE I
(Runs 1-14)

| Run No. | Temp. °C. | Collection Time, Min. | Phenanthrene Conv., % | Selectivity to | | | |
|---|---|---|---|---|---|---|---|
| | | | | 9,10-dihydro-phenanthrene | 1,2,3,4-tetra-hydrophen-anthrene | 1,2,3,4,5,6,7,8-octahydro-phenanthrene | perhydro-phenanthrene |
| 1 | 218 | 30 | 33.2 | 92.2 | — | 7.8 | — |
| 2 | 218 | 30 | 46.9 | 94.2 | 3.3 | 2.5 | — |
| 3 | 218 | 60 | 19.5 | 100 | — | — | — |
| 4 | 235 | 30 | 65.6 | 100 | — | — | — |
| 5 | 235 | 30 | 71.5 | 93.2 | 4.6 | 2.2 | — |
| 6 | 260 | 30 | 66.9 | 85.3 | 7.3 | 7.4 | — |
| 7 | 260 | 30 | 91.8 | 32.4 | 6.2 | 59.6 | 1.8 |
| 8 | 260 | 30 | 80.5 | 46.8 | 8.1 | 45.2 | — |
| 9 | 260 | 30 | 78.6 | 66.1 | 10.5 | 23.4 | — |
| 10 | 260 | 60 | 47.7 | 67.7 | — | 2.3 | — |
| 11 | 232 | 30 | 23.1 | 100 | — | — | — |
| 12 | 232 | 60 | 19.1 | 100 | — | — | — |
| 13 | 260 | 30 | 53.6 | 100 | — | — | — |
| 14 | 260 | 60 | 62.0 | 90.8 | 4.6 | 4.6 | — |

Catalyst A is seen to be selective in hydrogenating phenanthrene to its dihydro derivative. However, there appears to be no explanation for the large variances in the percent of phenanthrene converted for Runs 1 and 2; 6 and 7; 10 and 14 made at identical temperatures and collected within the same time frame. Except for Run 13, Table I shows that at temperatures below 260° C. the percent of phenanthrene converted is reduced, but that the percent of 9,10-dihydro phenanthrene, which is the desired product, is higher.

Example II (Runs 15-19)

Table II summarizes results of runs made with catalyst B. The runs were made at the same pressure ($3.55 \times 10^6$ Pa) and the same space rate (1.0 LHSV) as the preceding runs and all collected samples were thirty minute composites.

TABLE II
(Runs 15-19)

| Run No. | Temp., °C. | Phenanthrene Conv., % | Selectivity to | | | |
|---|---|---|---|---|---|---|
| | | | 9,10-dihydro-phenanthrene | 1,2,3,4-tetra-hydrophen-anthrene | 1,2,3,4,5,6,7,8-octahydro-phenanthrene | Unknown |
| 15 | 204 | 5.2 | 100 | — | — | — |
| 16 | 260 | 61.6 | 84.7 | 8.7 | 6.5 | — |
| 17 | 316 | 40.3 | 61.4 | 27.3 | 10.3 | 1.0 |
| 18 | 371 | 38.1 | 23.1 | 53.7 | 19.0 | 4.2 |
| 19 | 427 | 22.4 | 27.3 | 67.3 | 5.4 | — |

Catalyst B is also effective to hydrogenate selectively a polynuclear aromatic. Run 16, carried out at 260° C., resulted in the highest conversion of phenanthrene with good selectivity to the desired product. Under the conditions employed, it appears that with increasing temperatures products with a higher degree of saturation are produced.

Example III (Runs 20-23)

Table III summarizes results of other runs made with catalyst B that was sulfided prior to use. 20 mL of catalyst was treated for three hours at 400° C. with 15 percent hydrogen sulfide in hydrogen gas at a rate of 1200 LHSV (24 liters per hour). Then it was tested with the same feed at the same feed rate and pressure as in the preceding examples. During the sulfiding treatment much of the zinc that is present in zinc titanate becomes converted to zinc sulfide and it is believed that the rhenium promoter is converted to rhenium sulfide.

TABLE III (Runs 20-23)

| Run No. | Temp., °C. | Phenanthrene Conv., % | Selectivity | | |
|---|---|---|---|---|---|
| | | | 9,10-dihydro-phenanthrene | 1,2,3,4,-tetra-hydrophen-anthrene | 1,2,3,4,5,6,7,8-octahydro-phenanthrene |
| 20 | 204 | nil | — | — | — |
| 21 | 260 | 7.8 | 100 | — | — |
| 22 | 316 | 23.7 | 77.0 | 19.7 | 3.3 |
| 23 | 371 | 24.2 | 42.7 | 46.7 | 10.6 |

These data show that catalyst activity is reduced by the process of sulfiding and because of that higher temperatures are required for its use. However, runs 21 and 22 show that the catalyst retains selectivity to hydrogenate phenanthrene to its 9,10-dihydro pentanthrene derivative.

We claim:

1. A process comprising:
    contacting a polynuclear aromatic reactant with a zinc titanate catalyst under conditions to selectively hydrogenate the polynuclear aromatic reactant.

2. The process according to claim 1 wherein the catalyst is prepared by calcining a mixture of zinc oxide and titanium dioxide at a temperature within the range of from 650° to 1050° C.

3. The process according to claim 2 wherein the catalyst is calcined at a temperature in the approximate range of from 675° to 975° C.

4. The process according to claim 2 wherein the atomic ratio of zinc to titanium is within the range of from 1:1 to 3:1.

5. The process according to claim 2 wherein the atomic ratio of zinc to titanium is within the range of from 1.8:1 to 2:1.

6. The process according to claim 2 wherein the titanium dioxide has an average particle size of less than 100 millimicrons.

7. The process according to claim 2 wherein the titanium dioxide has an average particle size of about 30 millimicrons.

8. The process according to claim 2 wherein the catalyst is zinc orthotitanate.

9. The process according to claim 1 wherein the catalyst is promoted by a promoter selected from the group consisting of
    vanadium,
    chromium,
    nickel,
    molybdenum,
    tungsten,
    rhenium,
    platinum,
and combinations of any two or more thereof.

10. The process according to claim 9 wherein the promoter is rhenium.

11. The process according to claim 9 wherein the weight of promoter, expressed as an element and based on the total weight of catalyst plus promoter, is in the range of from 0.1 to 24 weight percent.

12. The process according to claim 9 wherein the concentration of any single promoter expressed as an element and based on the total weight of catalyst plus promoter is within the range of from 0.1 to 16 weight percent.

13. The process according to claim 12 wherein the concentration of any single promoter expressed as an element and based on the total weight of catalyst plus promoter is within the range of from 2 to 10 weight percent.

14. The process according to claim 10 wherein the concentration of rhenium expressed as an element and based on the total weight of the catalyst plus promoter is within the range of from 0.05 to 2 weight percent.

15. The process according to claim 1 wherein the polynuclear aromatic reactant is one having at least two aromatic nuclei and wherein at least two of the aromatic nuclei have two common carbon atoms.

16. The process according to claim 15 wherein the number of carbon atoms of the polynuclear aromatic reactant is within the range of from 10 to 40.

17. The process according to claim 15 wherein the polynuclear aromatic reactant is one having a molecular weight within the range of from 140 to 560.

18. The process according to claim 15 wherein the polynuclear aromatic reactant is selected from the group consisting of naphthalene, anthracene, phenanthrene, pyrene and naphthacene.

19. The process according to claim 15 wherein the polynuclear aromatic reactant is phenanthrene.

20. The process according to claim 1 wherein the temperature for the hydrogenation process is within the range of from 149° to 538° C. (300°-1000° F.).

21. The process according to claim 20 wherein the temperature for the hydrogenation process is within the range of from 204° to 371° C. (400°-700° F.).

22. The process according to claim 1 wherein the pressure for the hydrogenation process is within the range of from $1.48 \times 10^6$ to $20.8 \times 10^6$ Pa.

23. The process according to claim 22 wherein the pressure for the hydrogenation process is within the range of from $2.86 \times 10^6$ to $6.9 \times 10^6$ Pa.

24. The process according to claim 1 wherein the quantity of hydrogen combined with the reactant is within the range of from 100 to 10,000 SCF/bbl of reactant.

25. The process according to claim 24 wherein the quantity of hydrogen combined with the reactant is within the range of from 500 to 3000 SCF/bbl of reactant.

26. The process according to claim 1 wherein the contact time of the reactant with the catalyst is within the range of from 0.1 to 20 LHSV.

27. The process according to claim 26 wherein the contact time of the reactant with the catalyst is within the range of from 0.5 to 5 LHSV.

28. The process according to claim 9 wherein the promoter is platinum present in a concentration within the range of 0.05 to 2 weight percent.

29. The process according to claim 9 wherein the vanadium promoter, if present, is derived from the group of vanadium compounds consisting of di-, tri-, tetra-, and pentavalent vanadium oxides, vanadium (III) sulfide, vanadium (IV) oxide sulfate, ammonium metavanadate, and sodium metavanadate; the chromium promoter, if present, is derived from the group of chromium compounds consisting of ammonium chromate, ammonium dichromate, chromic nitrate, chromium (III) oxide, chromium (VI) oxide, chromic sulfate, potassium chromate, potassium dichromate, and chromic acetate; the nickel promoter, if present, is derived from the group of nickel compounds consisting of nickel acetate, nickel carbonate, nickel nitrate, nickel oxide, nickel sulfate, ammonium nickel sulfate, and nickel sulfamate; the molybdenum promoter, if present, is derived from the group of molybdenum compounds consisting of ammonium molybdate, ammonium heptamolybdate, sodium molybdate, potassium molybdate, molybdenum oxide, and molybdenum sulfide; the tungsten promoter, if present, is derived from the group of tungsten compounds consisting of ammonium metatungstate, ammonium paratungstate, tungsten (IV) oxide, tungsten (VI) oxide, tungsten (IV) sulfide, tungsten (VI) sulfide, tungstophosphoric acid, and tungstosilicic acid; the rhenium promoter, if present, is derived from the group of rhenium compounds consisting of perrhenic acid, ammonium perrhenate, rhenium (VI) oxide, rhenium (VII) oxide, and rhenium sulfide; and the platinum promoter, if present, is derived from the group of platinum compounds consisting of diamineplatinum (II) nitrate and tetraamineplatinum (II) nitrate.

* * * * *